(12) United States Patent
Nordstrom

(10) Patent No.: US 8,444,270 B2
(45) Date of Patent: May 21, 2013

(54) AUTO-PHOROPTER INTERFACE AND COMPUTER MONITOR FILTER

(76) Inventor: Steven B. Nordstrom, Hinsdale, IL (US)

( * ) Notice: Subject to any disclaimer, the term of this patent is extended or adjusted under 35 U.S.C. 154(b) by 487 days.

(21) Appl. No.: 12/602,215

(22) PCT Filed: May 30, 2008

(86) PCT No.: PCT/US2008/006894
§ 371 (c)(1),
(2), (4) Date: May 27, 2010

(87) PCT Pub. No.: WO2008/150476
PCT Pub. Date: Dec. 11, 2008

(65) Prior Publication Data
US 2010/0265462 A1    Oct. 21, 2010

Related U.S. Application Data

(60) Provisional application No. 60/940,810, filed on May 30, 2007, provisional application No. 60/965,010, filed on Aug. 16, 2007.

(51) Int. Cl.
*A61B 3/02*    (2006.01)

(52) U.S. Cl.
USPC .......................................... 351/223; 351/222

(58) Field of Classification Search
USPC ................. 351/200, 205, 209–211, 216, 222, 351/223
See application file for complete search history.

(56) References Cited

U.S. PATENT DOCUMENTS

| 4,861,156 | A | * | 8/1989 | Terry ............................. 351/243 |
| 5,568,209 | A | * | 10/1996 | Priester et al. ................ 351/243 |
| 5,757,542 | A | * | 5/1998 | Brock ........................... 359/390 |
| 2006/0023163 | A1 | | 2/2006 | Foster |
| 2006/0050238 | A1 | | 3/2006 | Nakamura |
| 2007/0019272 | A1 | | 1/2007 | Hillis et al. |
| 2008/0198328 | A1 | * | 8/2008 | Seriani et al. ................. 351/205 |

FOREIGN PATENT DOCUMENTS

| CA | 2214260 A1 | 2/1999 |
| DE | 4124056 A1 | 1/1993 |

* cited by examiner

*Primary Examiner* — Thomas K Pham
*Assistant Examiner* — Brandi Thomas
(74) *Attorney, Agent, or Firm* — Bishop & Diehl, Ltd.

(57) ABSTRACT

An interface for allowing communication between an auto-phoropter and a computer with visual acuity testing software. An adjustable filter for a computer monitor used with a computer with visual acuity testing software.

4 Claims, 7 Drawing Sheets

AUTO-PHOROPTER INTERFACE AND COMPUTER MONITOR FILTER

RELATED APPLICATIONS

This application claims the benefit of U.S. Provisional Application No. 60/940,810 filed May 30, 2007 and U.S. Provisional Application No. 60/965,010 filed Aug. 16, 2007 the entireties of which are incorporated herein.

TECHNICAL FIELD

The present invention relates, in general, to automated auto-phoropters and automated visual acuity testing systems and more particularly to an interface between an auto-phoropter and an automated visual acuity testing system. In addition, the present invention relates to a Mesoptic filter for a monitor for a computer with an automated visual acuity testing system.

BACKGROUND

Currently in the field of ophthalmology and optometry, automated systems are used to control auto-phoropters, chart projectors, and other equipment providing increased efficiency in the exam, including the capture and transfer of data to electronic medical records. Chart projectors are limited in their use, however, as they have a finite number of tests available, require considerable maintenance and cannot present randomized eye charts. Since the automated phoropters are new technology and relatively expensive, practitioners often objected to using older outdated chart projectors in combination with more sophisticated new technology. There also exists a strong movement in the industry to migrate away from chart projectors in favor of more sophisticated computerized visual acuity systems, and a resulting need for the integration between auto-phoropters, computerized visual acuity and other equipment.

Currently available auto-phoropters include: RT-5100 Auto-Phoropter sold by MARCO of Jacksonville, Fla. and made by NIDEK of Japan; RT-2100 Auto-Phoropter sold by MARCO Jacksonville, Fla. and made by NIDEK of Japan; and, CV-5000 sold by TOPCON of Japan. In addition, currently available automated visual acuity testing systems include the PROVIDEO® sold by Innova Systems, Inc. of Burr Ridge, Ill.

In addition to the above, for clinical trials on many new ophthalmic products, particularly those requiring contrast sensitivity testing, the FDA requires vision analysis to be conducted at both photopic and mesopic light levels. In some cases, scotopic levels are also required. Photopic levels are high light levels where primarily the cones of the retina are the primary light receptors. Mesopic levels are low-intermediate light levels where both the rods and cones of the retina serve as the light receptors. Scotopic levels are very dim conditions where only the rods of the retina serve as the light receptors.

The requirements for many vision tests are very precise and require specific light levels of 85 candela per square meter for photopic measurement; 3-4 candela per square meter for mesopic measurement; and less than 2 candela per square meter for scotopic levels.

With traditional vision testing methods, these levels were achieved by either controlling the illumination of a vision testing chart or by controlling the luminance of a light box device. With computerized vision testing, it is not possible to accurately produce these light levels in a consistent, repeatable manner using a standard CRT or LCD monitor.

One problem associated with the difficulty achieving correct light levels is the inability to produce the many shades of grey required for contrast testing if the light output of the monitor is reduced. The brightness of the monitor may not be used to control the light level, because the quality of the image is reduced with reduced brightness and it is very tedious to restore the monitor to its original settings for subsequent tests. Reducing the light level by making the background a darker shade of grey reduces the number of grey shades available for test optotypes by 255 minus the value of the grey shade used for the background. The obvious solution of placing a filter over the monitor screen is inadequate because of the lack of accurate, stable filter densities and the difficulty of calibrating the monitor/filter combination to the correct light level.

BRIEF SUMMARY

Communication with an auto-phoropter, which was designed to communicate with a standard ophthalmic chart projector, is accomplished via a high-speed series of voltage pulses of varying widths. These pulses represent unique codes corresponding to the chart or screen to be displayed but, they cannot be directly interpreted by a standard data interface on the computer, which may also contain software for an automated visual acuity testing system.

Instead of sending and receiving data in "bytes" or "words", the information is sent as a series of voltage pulses of varying duration. Computer software, specifically interface software, can detect these as "state changes", a change from high (5V) to low (less than 3V), on any line that can be directly read and controlled on the computer's RS-232 or USB port. The auto-phoropter receive line can also be connected to any unused line on the RS-232 or USB port that can be directly controlled by software, specifically the interface software. Changing the state of the selected line rapidly from 5V to 0V appears as a series of voltages pulses of the correct format to the auto-phoropter receive line.

Communications between the computer and the auto-phoropter can be accomplished with an interface that uses any combination of lines on the RS-232, USB, parallel port or any other available external connection to the computer which can be controlled at a high rate of speed by the interface software, running on the computer, except the RS-232 transmit or receive lines.

Additionally, it is contemplated that the interface between the auto-phoropter and computer which contains software for an automated visual acuity testing system is wireless. The wireless interfaces on an auto-phoropter send an infrared signal at a standard infrared frequency containing the same pulsed signal as described above in relation to the wired interface. The interface software on the computer contains a complete database of these signals and the incoming signal is compared to the codes contained in the database to determine what screen to display or what action is necessary.

The desired action, in the form of a command, is sent by the interface software to the vision testing system software for execution of the command.

By establishing a database containing the signals from devices made by several manufacturers, the present embodiment of this invention has the capability of accepting infrared signals simultaneously from equipment made by different manufacturers or working with any supported manufacturer without the need to pre-configure the system.

The interface between auto-phoropter control unit and computerized visual acuity allows the auto-phoropter to be used in conjunction with the additional tests, randomization, and additional interfaces of the automated visual acuity testing system.

The automated visual acuity testing system can be controlled by the auto-phoropter control unit as well as the automated visual acuity testing system remote control. Charts not currently available on the auto-phoropter's control unit may be accessed directly with the automated visual acuity testing system remote control. Signals from either unit may be received at the same time, never limiting the tests or interfaces available to the doctor.

In an embodiment, the auto-phoropter/computerized visual acuity system interface consists of both wired and infrared remote versions. One source of signals stems from the auto-phoropter control unit when specific chart buttons are activated. The signals are intercepted by the vision testing system. Both versions transfer binary codes to the vision testing system to trigger a computerized chart display. The binary signal is decoded and controls the computerized visual acuity chart display. One or more button pushes on the auto-phoropter control unit may be used to trigger a single event on the computerized chart display.

The present invention also provides nearly infinite adjustment to the light output of the vision testing system by incorporating a filter of variable density. The filter is composed of a large sheet of linearly polarized filter material affixed to the face of the monitor. To this filter is affixed a rotatable (circular) sheet of linearly polarized filter material. When the moveable sheet is rotated, the light passing through the two sheets of filter material can be accurately controlled in intensity. The filter can be calibrated to any desired density by rotating the moveable sheet and measuring the light transmission with a standard photometer.

DETAILED DESCRIPTION

Figure 1:
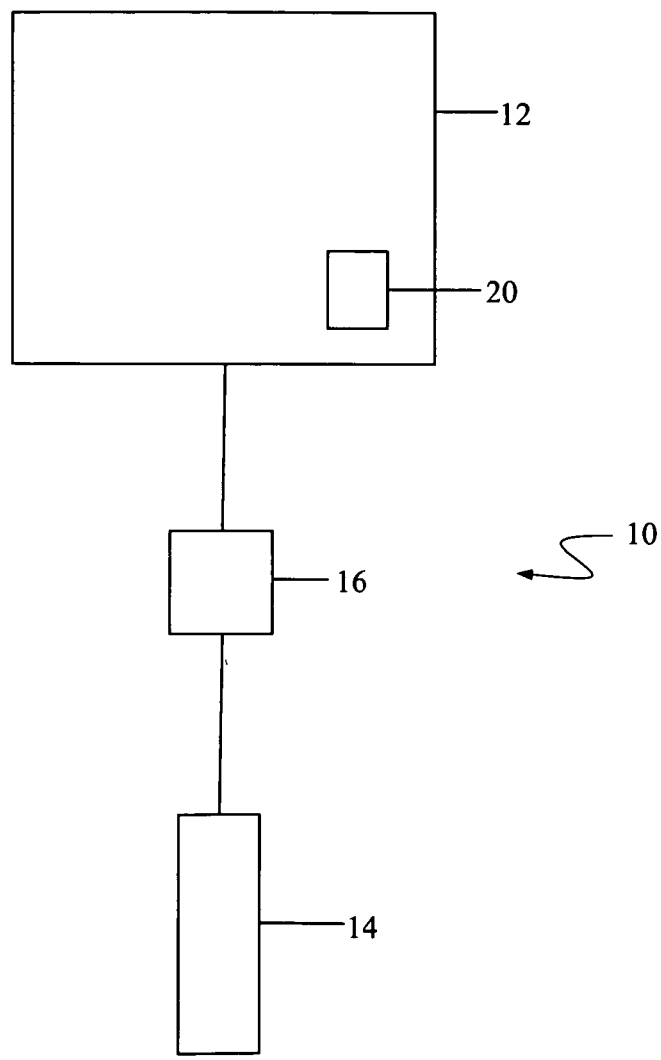
FIG. 1 is a view of a first embodiment of the present invention.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

In the following description, numerous specific details are provided to provide a thorough understanding of embodiments of the invention. One skilled in the relevant art will recognize, however, that the invention can be practiced without one or more of the specific details, or with other methods, components, materials, and so forth.

Without further elaboration, it is believed that one skilled in the art can use the preceding description to utilize the present disclosure to its fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles of the disclosure provided herein. In other words, various modifications and improvements of the embodiments specifically disclosed in the description above are within the scope of the appended claims. Note that elements recited in means-plus-function format are intended to be construed in accordance with 35 U.S.C. §112 ¶6. The scope of the invention is therefore defined by the following claims.

Auto-Phoropter Interface

As depicted in FIG. 1, a first embodiment of the invention 10 includes an auto-phoropter 12, a computer 14 with visual acuity testing software, and an interface 16. In this embodiment the auto-phoropter is an RT-5100.

Figure 2:
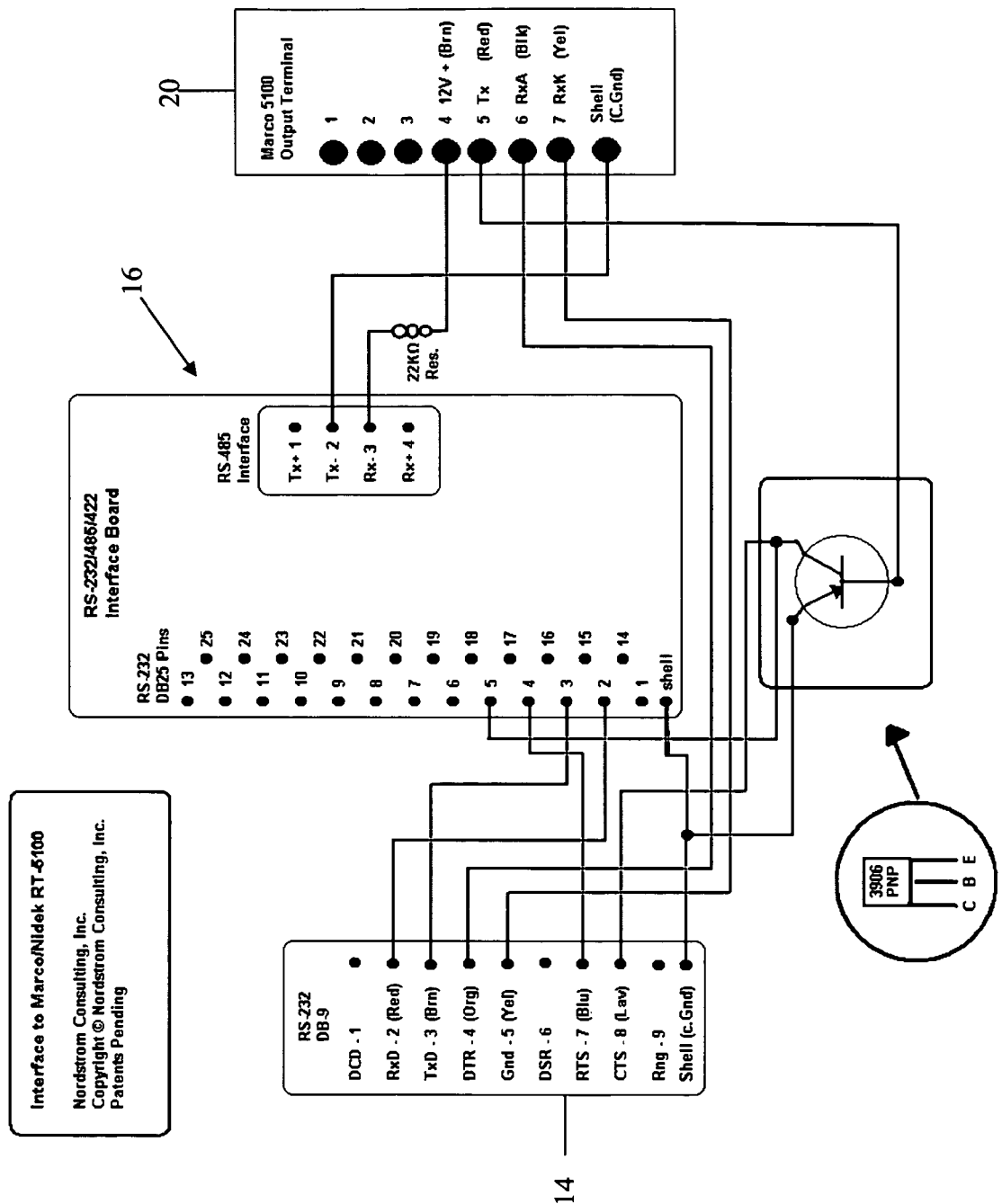
FIG. 2 is an electrical diagram of an interface for the first embodiment of the present invention.
Figure 3:
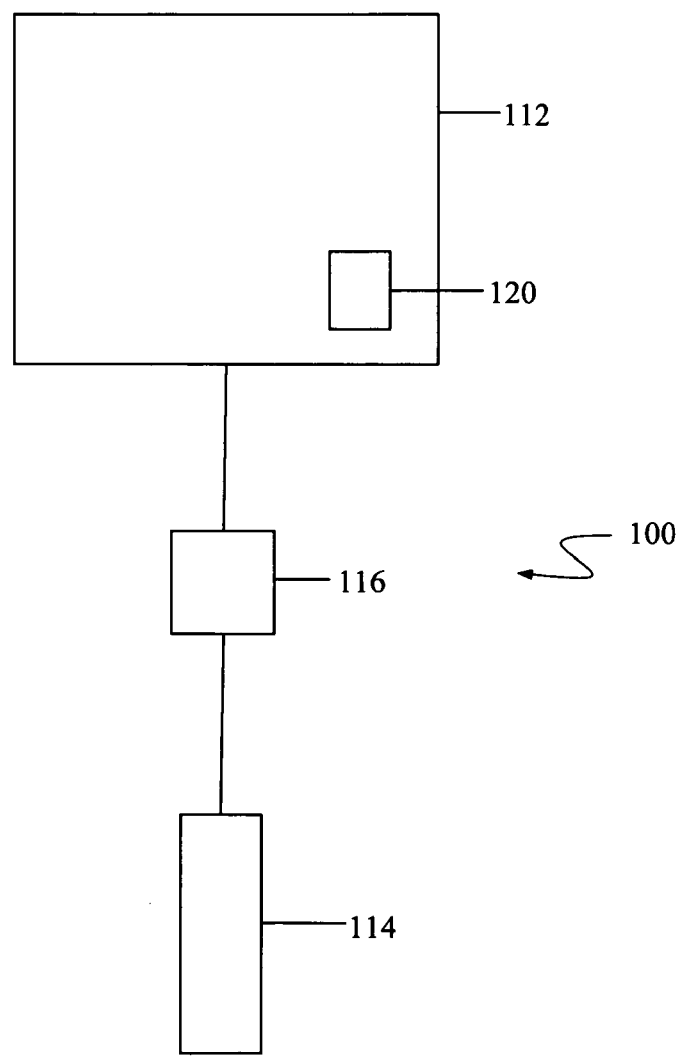
FIG. 3 is a view of a second embodiment of the present invention.

The auto-phoropter 12 includes a connection port 20. As shown in FIG. 2, connection port 20 has the following connections:

Pin 1—GND
Pin 2—IR_Rx (Infrared—not used in this embodiment)
Pin 3—IR_Tx (Infrared—not used in this embodiment)
Pin 4—+12 volts
Pin 5—W_Tx (wired)

Pin 6—W_RxA (wired)
Pin 7—W_RxK (wired)
Pin E—Frame Gnd

The interface 16 of this embodiment includes the following connections between connection port 20 of the auto-phoropter 12 and the computer 14, as shown in detail in FIG. 2.

The 12V line (pin 4) from the connection port 20, is connected to the Rx-terminal on an Aten IC-485SN RS485 to RS232 converter. This causes the RS-485 to RS-232 board to maintain a RS-232 pin 5 (25 pin configuration—CTS) at 5 volts which is then connected to the collector pin of the 3906 PNP transistor.

The W_Tx line (pin 5) from the connection port 20, is connected to the base terminal of the 3906 PNP transistor which is used as a switching transistor in this embodiment of the invention. This completes a current loop between pin 4 (12v) and pin 5 (W_Tx) of the connection port 20.

The W_RxA (pin 6) from the connection port 20 is connected directly to the RS-232 DTR (data terminal ready—pin 4) on the RS-232 connection of the computer 14.

The W_RxK (pin 7) from the connection port 20 is connected directly to the RS-232 GND (signal ground—pin 5) connection of the computer 14.

The Shell or "frame ground" (pin E) from the connection port 20 is connected to the Rx-terminal on the Aten IC-485SN RS-485 to RS-232 converter.

The interface 16 is then completed by connecting the Shell pin from the computer 14 to the Shell (pin E) of the Aten IC-485 RS-485 to RS-232 converter which, in turn, is connected to the Shell (frame ground) of the connection port 20 through the Tx-terminal of the RS-485 to RS-232 converter.

A pulsed signal is provided to the computer 14 by connecting the emitter terminal of the 3906 PNP transistor to the Shell (frame ground) on the RS-232 connection of the computer 14, and, by connecting the collector of the 3906 PNP transistor to the CTS (clear to send line—pin 8) on the RS-232 connection of the computer 14.

The signal is received by the computer 14 by timing the changes in "state" of the computer's CTS line on the RS-232 interface which is connected through the 3906 PNP transistor to the W_Tx (wired transmit) line of the connection port 20.

Signals are transmitted by the computer 14 to the auto-phoropter 12 by rapidly changing the "state" of the RS-232 DTR line of the computer 14 which is connected directly to the W_RxA (wired receive) line of the connection port 20.

Since the Aten IC-485SN RS-485 to RS-232 converter is used to provide a low voltage current loop from the 12v line of the connection port 20 to the W_Tx (wired transmit) line of the connection port 20, the RS-485 to RS-232 converter is not essential to this embodiment of the present invention and the wired interface used in the second embodiment may be freely substituted with no change in performance.

A second embodiment of the present invention 100 also includes an auto-phoropter 112, a computer 114 with visual acuity testing software, and an interface 116. In this embodiment the auto-phoropter is an RT-2100.

Figure 4:
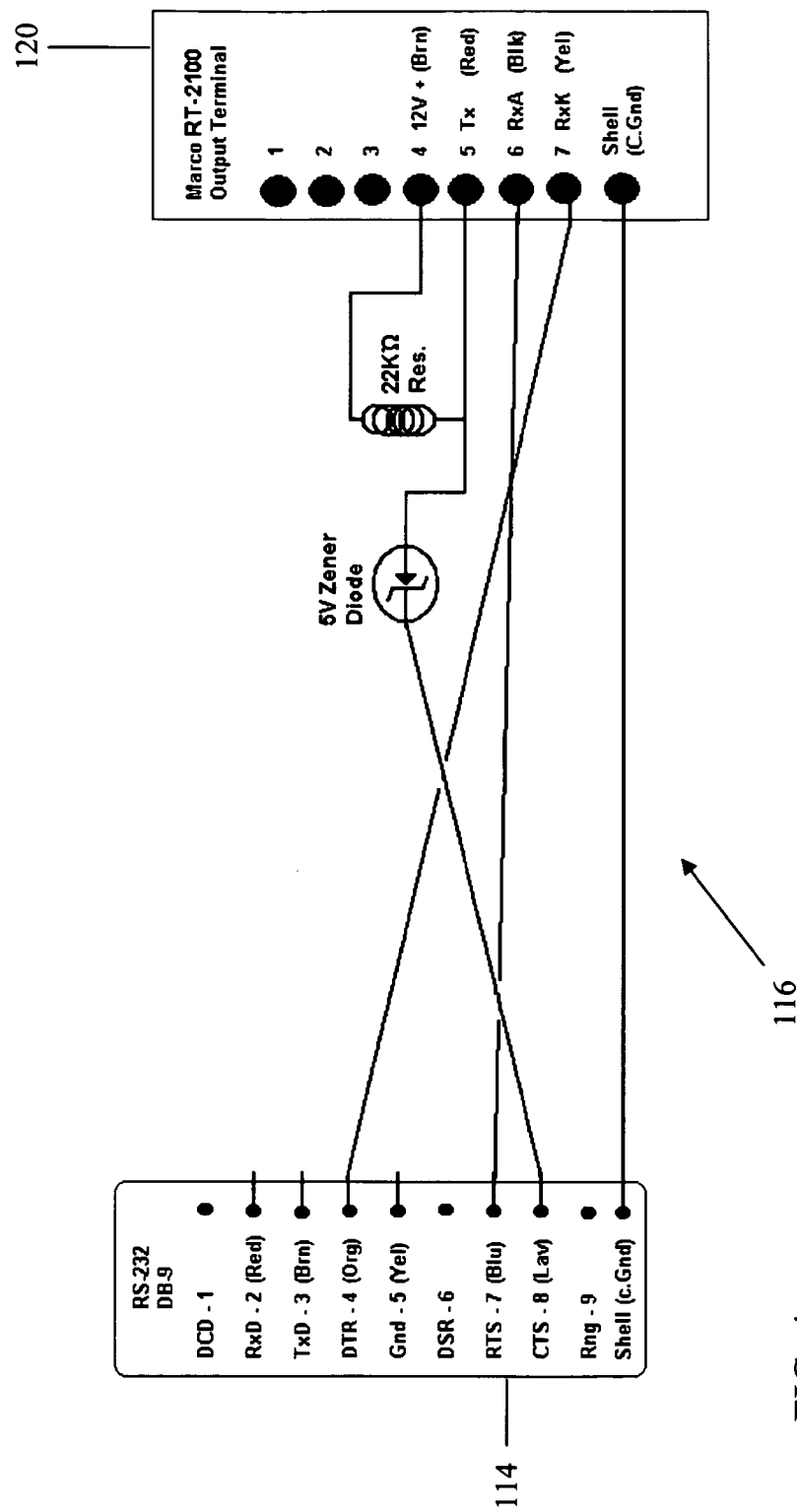
FIG. 4 is an electrical diagram of an interface for the second embodiment of the present invention.

The auto-phoropter 112 includes a connection port 120. As shown in FIG. 4, connection port 120 has the following connections:

Pin 4—+12 volts
Pin 5—W_Tx (wired)
Pin 6—W_RxA (wired)
Pin 7—W_RxK (wired)
Pin E—Frame Gnd The interface 116 of this embodiment includes the following connections between connection port 120 of the auto-phoropter 112 and the computer 114, as shown in detail in FIG. 4.

The 12V line (pin 4) from the connection port 120, is connected to a 2200 Ohm resistor the opposite end of which is connected to pin 5 the W_Tx (wired transmit) line on the connection port 120, creating a current loop between the two terminals.

The W_Tx line (pin 5) from the connection port 120, in addition to the connection to pin 6 (12v) through the 2200 Ohm resistor, is connected to the anode end of a 5v Zener diode.

The W_RxA (pin 6) from the connection port 120 is connected directly to the RS-232 RTS (request to send—pin 7) on the RS-232 connection of the computer 114.

The W_RxK (pin 7) from the connection port 120 is connected directly to the RS-232 DTR (data terminal ready—pin 4) connection of the computer 114.

The Shell or "frame ground" from the connection port 120 is connected to the Shell or "frame ground" of the RS-232 connection of the computer 114.

To complete the circuit, the CTS (clear to send) line on the RS-232 connection (pin 8) of the computer 114 is connected to the cathode of the Zener diode.

To receive a series of pulses from the auto-phoropter 112, a signal is sent from the connection port 120 Tx line (pin 5 on the connection port 120) by pulsed voltage drops on the 12v to Tx current loop. The voltage drops on the current passing through the Zener diode cause the signal received by the computer 114 to appear as a series of voltage "pulses". These pulses change the state of the RS-232 CTS line on the computer 114 which is detected by interface software installed on the computer 114. The interface software records each occurrence of a change in state on the RS-232 CTS line and calculates the duration of the pulses based on the recorded data. Using the known number and format of pulses associated with each command, the interface software collects several samples of the command to eliminate erroneous responses from the visual acuity system. Once several commands have been received from the auto-phoropter controller, a return code, indicating successful communication, is sent to the auto-phoropter in the manner described in the following paragraph.

To transmit a signal from the computer 114 to the auto-phoropter 112, the RTS (request to send—pin 7) line of the computer 114 is rapidly changed by the Provideo AutoLink interface software. The RTS line from the computer 114 is connected directly to the RxA (receive) line on the connection port 120 which receives the signal from the computer 114 as a series of voltage pulses.

In addition to the above embodiments, the present invention contemplates a "wireless" interface between an auto-phoropter and a computer. In this embodiment, the invention may include an auto-phoropter 200, an infrared transmitter 202 communicating with the auto-phoropter 200, an infrared receiver 204 and a computer 206 communicating with the infrared receiver 204. The computer 206 includes visual acuity testing software and interface software.

Mesopic Filter for Computerized Visual Acuity

The present invention depends on the fact that when one looks through a filter consisting of two sheets of transparent linearly polarized material, if the axis of polarization of both sheets is parallel, the filter appears to be completely transparent and, if the axis of polarization of the two sheets are at a 90° angle, the filter appears to be completely opaque.

Figure 5:
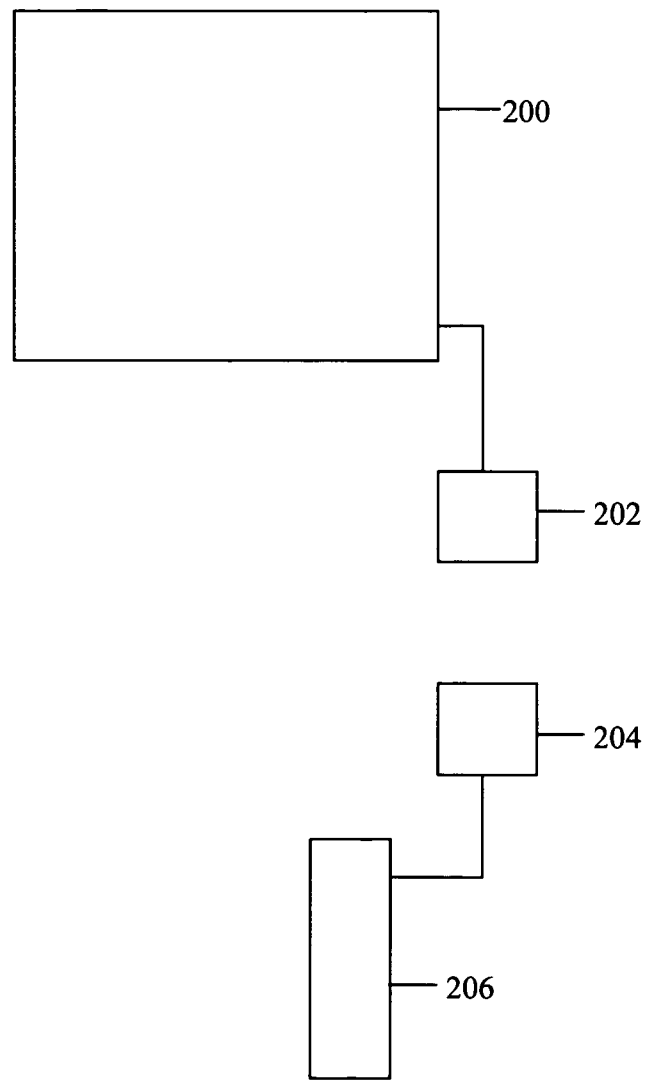
FIG. 5 is a view of a wireless embodiment of the present invention.
Figure 6:
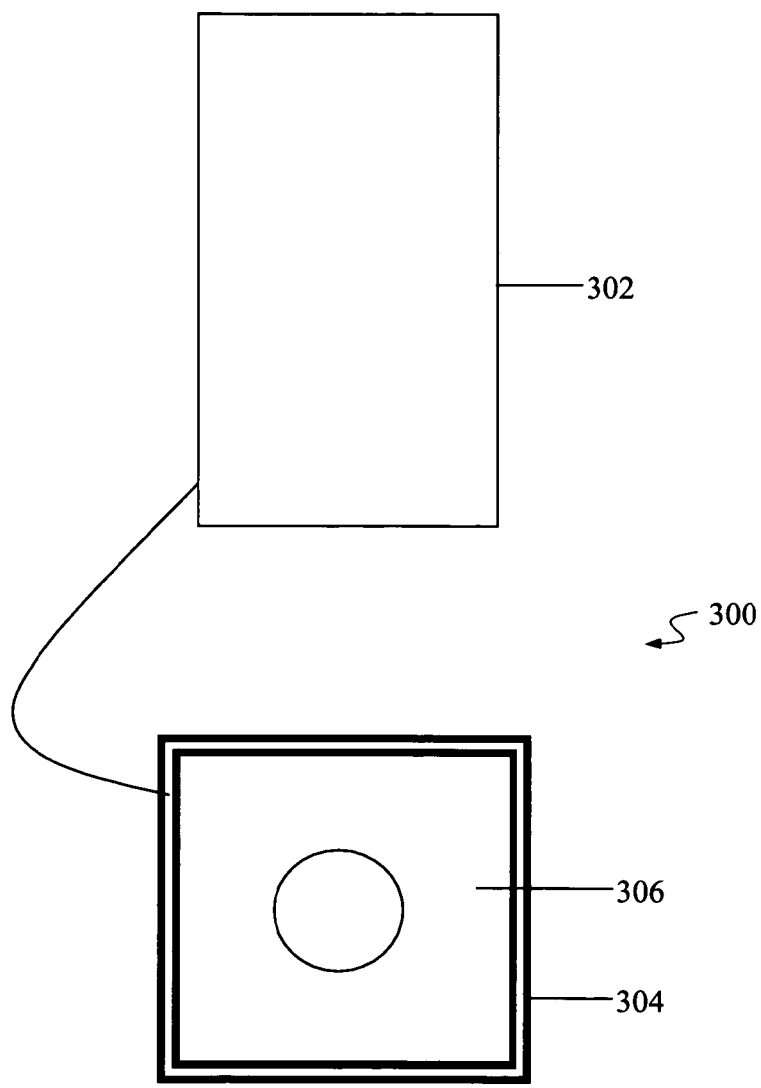
FIG. 6 is a view of a filter according to the present invention.
Figure 7:
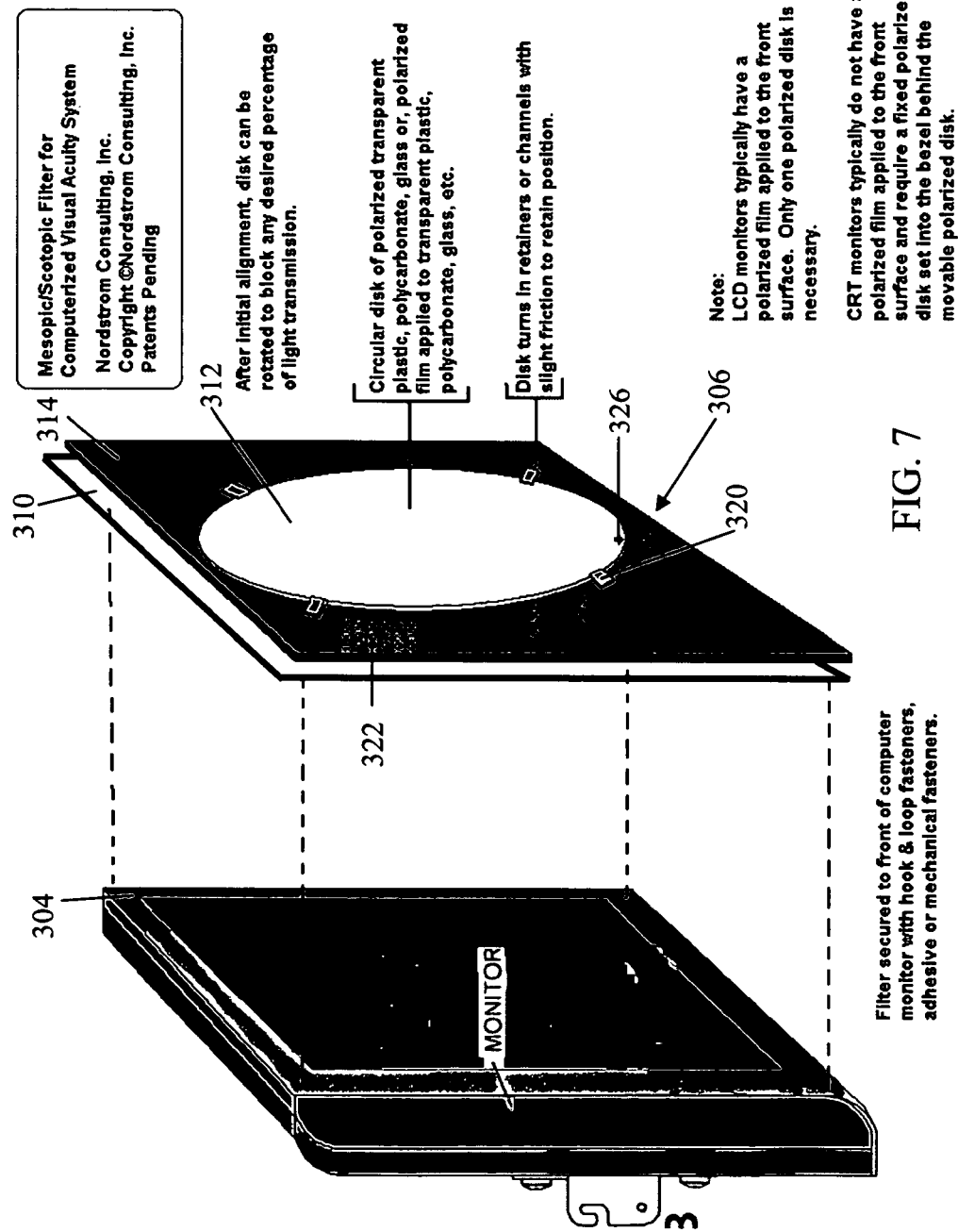
FIG. 7 is an alternate view of a filter according to the present invention.

This embodiment of the present invention 300 (depicted in FIGS. 5 and 6) includes a computer 302, a monitor 304 and a filter 306. The computer 302 includes visual acuity testing software. The monitor 304 can be a CRT monitor or an LCD monitor. A CRT monitor does not typically have a polarized filter applied to the front surface of the viewing area. A first embodiment of the filter 306 for this application (where the monitor does not already include a polarized filter) includes two sheets of polarized filter material 310, 312 and a frame 314. It is preferred that the front sheet 312 is a circle of the largest possible diameter that will fit within the viewing area of the monitor 304. The frame 314 for the circular transparent portion should be opaque and sized to cover the entire viewing area plus a margin large enough to attach to the monitor 304 via hook and loop fasters, clips, tabs, buttons or any other fasteners. Alternatively, it is possible to use a rectangular sheet of the polarized material and paint, laminate or otherwise block light from passing through all but a circle in the center of the correct diameter and thus the back sheet 310 and the frame 314 will be made of the same sheet of material.

The front sheet 312 is attached over the center of the back sheet 310 and held in place by a bezel 320, channel or retainer that allows the front sheet 312 to be rotatable with respect to the back sheet 310. With the filter 306 mounted, the monitor 304 may be calibrated to allow whatever light level is desired at the transparent setting with the axis of polarization of both sheets of filter material parallel. The rotatable sheet 312 may then be rotated from 0 to 90 degrees to allow transmission of light at any percentage from 100% to 0%. Calibration marks 322 may be printed on the frame 314 with an alignment mark 326 on the first sheet 312 at precise settings established by measuring the light transmission with a photometer.

A monitor 304 can also be an LCD monitor which usually has a polarized filter applied to the front surface of the viewing area. An embodiment of the filter 306 for this application (wherein the monitor already has a polarized filter) comprises the same as described above, with the exception that the filter 306 need not include the rear sheet 310. Adjustment and calibration are then identical to the above filter described for CRT monitors.

Computerized Visual Acuity System Interface with Electronic Medical Records

The auto-phoropter writes data to a file which is transferred to electronic medical records (EMR) as a XML file. The interface between the auto-phoropter and the computer with visual acuity testing software allows additional information to be stored for EMR transfer, such as specific tests performed or patient education materials presented to the patient. The computer with visual acuity testing software transfers the data in a medical standard format (DICOM) so that it may interface with any electronic medical records software package.

Auto Calibration for Computerized Visual Acuity

For vision testing in research and clinical trials, including contrast testing, the FDA requires the white value of any vision testing device to be 85 candela per square meter +/−20%. The current standard for vision testing for research and clinical trials is a light box with translucent vision testing charts illuminated from within by a calibrated light source.

Contrast for vision testing is defined as $(a-b)/(a+b)$ where a is the white value and b is the difference between the dark and light values. In computerized contrast testing, the darker values must be selected from the shades of pure gray that the computer/monitor combination is capable of producing. A 16 million color monitor has 255 shades of pure gray. In order to produce accurate contrast, the darker value must be correctly identified from among the 255 shades of gray available.

The preferred method of calibrating a specific contrast for a vision test presentation is to measure and pre-calculate contrast levels prior to displaying any contrast testing screen. This is done by measuring the light and dark values produced by the monitor with a photometer and selecting the shade of gray that produces the desired contrast level, based on the above formula.

The present invention uses a photometer connected to the computer through a serial or USB port which supplies measured light levels to software that automatically selects a shade of gray which most closely matches each of the desired contrast levels. The software cycles through every shade of gray that the computer/monitor is capable of producing and selects the best shade of gray for each of the desired contrast levels.

Although the traditional sequence of contrasts is represented by a logarithmic progression of values, this is not usually possible using contemporary microcomputer/monitor combinations. Once the system has established the gray shades that most closely match the target values, it will then calculate the actual contrast values and use these for calculating the patient's contrast threshold.

In-Field Calibration for Computerized Visual Acuity

Computer monitors vary in both light output and contrast levels over time. For clinic trials, the FDA requires daily verification of the systems calibration. Therefore, there is a need for in-field calibration where the technician can verify the contrast levels and, when needed, automatically adjust the contrast levels to fit the sample readings.

The technician measures selected contrast levels (several) to verify the calibration of the system prior to conducting contrast tests. If the contrast measurements do not match the recorded calibration settings for the sample contrast level, the contrast curve and each of the gray shade assignments are adjusted by the software to fit the sample readings.

Without further elaboration, it is believed that one skilled in the art can use the preceding description to utilize the present disclosure to its fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles of the disclosure provided herein. In other words, various modifications and improvements of the embodiments specifically disclosed in the description above are within the scope of the appended claims. Note that elements recited in means-plus-function format are intended to be construed in accordance with 35 U.S.C. §112 ¶6. The scope of the invention is therefore defined by the following claims.

The invention claimed is:

1. An apparatus comprising:
   an auto-phoropter;
   a computer including visual acuity testing system software; and,
   an interface comprising an RS-232 port and an RS-485 interface, the interface for communicating between the auto-phoropter and the computer; and
   a transistor connected to the interface, the computer and a Tx terminal of the auto-phoropter;
   wherein, the RS-232 port is connected to the computer and the RS-485 interface is connected to the auto-phoropter.

2. The apparatus of claim 1 wherein the interface is a wired interface.

3. The apparatus of anyone of claim 1 or 2 further comprising interface software on the computer.

4. An apparatus comprising:
an auto-phoropter for use in testing visual acuity
a computer including visual acuity testing software; and
an interface for communicating between the auto-phoropter and the computer, the interface comprising:
   a zener diode connected to the computer and a Tx output of the auto-phoropter; and,
   a resistor connected to a 12V+, the Tx of the auto-phoropter and the zener diode.

* * * * *